United States Patent [19]

Bundy

[11] 4,029,814

[45] June 14, 1977

[54] PHENYL-SUBSTITUTED PROSTAGLANDIN-E TYPE ANALOGS

[75] Inventor: Gordon L. Bundy, Portage, Mich.

[73] Assignee: The Upjohn Company, Kalamazoo, Mich.

[22] Filed: Sept. 22, 1976

[21] Appl. No.: 725,549

Related U.S. Application Data

[60] Continuation-in-part of Ser. No. 645,279, Dec. 29, 1975, abandoned, which is a division of Ser. No. 431,011, Jan. 7, 1974, Pat. No. 3,987,087, which is a continuation-in-part of Ser. No. 167,446, July 29, 1971, abandoned, which is a continuation-in-part of Ser. No. 86,303, Nov. 2, 1970, abandoned.

[52] U.S. Cl. .............................. 424/308; 260/240 R; 260/340.9; 260/343.6; 260/408; 260/410; 260/410.5; 260/413; 260/456 R; 260/410.9 V; 260/520 B; 424/305

[51] Int. Cl.$^2$ ........................................ C07C 49/28
[58] Field of Search ........... 260/473 A; 260/473 A, 260/410.9; 424/308, 305

[56] References Cited

FOREIGN PATENTS OR APPLICATIONS 7,301,094  7/1973  Netherlands ................. 260/473 A Primary Examiner—Paul J. Killos
Attorney, Agent, or Firm—Morris L. Nielsen

[57] ABSTRACT

This invention is a group of phenyl-substituted PGE-type, PGF-type, PGA-type and PGB-type compounds, and processes for making them. These compounds are useful for a variety of pharmacological purposes, including anti-ulcer, inhibition of platelet aggregation, increase of nasal patency, labor inducement at term, and wound healing.

148 Claims, No Drawings

PHENYL-SUBSTITUTED PROSTAGLANDIN-E TYPE ANALOGS

CROSS REFERENCE TO RELATED APPLICATIONS

This is a continuation-in-part of copending application Ser. No. 645,279 filed Dec. 29, 1975, now abandoned which was a division of then copending application Ser. No. 431,011 filed Jan. 7, 1974 now issued as U.S. Pat. No. 3,987,087 which was a continuation-in-part of then copending application Ser. No. 167,446, filed July 29, 1971, now abandoned, which was a continuation-in-part of then copending application Ser. No. 86,303 filed Nov. 2, 1970, now abandoned.

DESCRIPTION OF THE INVENTION

This invention relates to compositions of matter, and to methods and intermediates for producing them. The several aspects of this invention relate to novel analogs of some of the known prostaglandins, for example, prostaglandin $E_1$ ($PGE_1$), prostaglandin $E_2$ ($PGE_2$), prostaglandin $F_1$ ($PGF_{1\alpha}$ and $PGF_{1\beta}$), prostaglandin $F_2$ ($PGF_{2\alpha}$ and $PGF_{2\beta}$), prostaglandin $A_1$ ($PGA_1$), prostaglandin $A_2$ ($PGA_2$), prostaglandin $B_1$ ($PGB_1$), prostaglandin $B_2$ ($PGB_2$), and the dihydro derivatives of $PGE_1$, $PGF_{1\alpha}$, $PGF_{1\beta}$, $PGA_1$, $PGB_1$, to novel methods for producing those novel prostaglandin analogs, and to novel chemical intermediates useful in those novel methods. In particular, the novel prostaglandin analogs of this invention are phenyl-substituted in the C-13 to C-20 chain.

The essential material for this application, including the background of the invention, the disclosure of the invention, and the description of the preferred embodiments, including Preparations and Examples, is incorporated by reference from pending and commonly owned U.S. Pat. application Ser. No. 431,011, filed Jan. 7, 1974, now U.S. Pat. No. 3,987,087 under the provisions of M.P.E.P. 608.01(p).

SUMMARY OF THE INVENTION

It is the purpose of this invention to provide novel prostaglandin analogs, and processes for making them.

The novel prostaglandin analogs of this invention each have a benzene ring as part of the C-13 to C-20 chain of the prostanoic acid structure (1) acid or 8-isoprostanoic acid structure (VII). That benzene ring is present as a substituent or unsubstituted phenyl moiety (1) attached as a substituent replacing one of the hydrogens on one of the methylenes between C-15 and the terminal methyl of the prostanoic acid or 8-isoprostanoic acid structure or (2) attached to the terminal or omega carbon of the C-16 to C-20 portion of the chain, replacing either (a) one of the hydrogens of the terminal methyl, (b) the entire terminal methyl, or (c) the terminal methyl plus one to four of the methylenes adjacent to that terminal methyl. For example, two of the novel prostaglandin analogs of this invention are represented by the formulas:

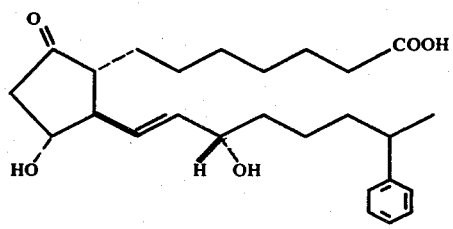

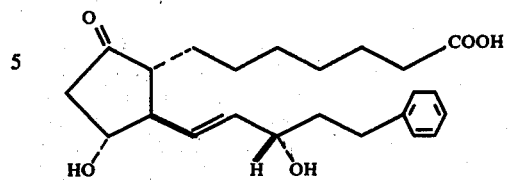

Based upon its relationship to $PGE_1$, and prostanoic acid, the compound of Formula VIII is named 19-phenyl-$PGE_1$, and that of Formula IX is named 17-phenyl-18,19,20-trinor-$PGE_1$. In Formula IX "trinor" indicates absence of the terminal $-CH_2-CH_2-CH_3$ of $PGE_1$.

Each of the novel phenyl-substituted prostaglandin analogs of this invention is encompassed by one of the following formulas or by the combination of that formula and its mirror image:

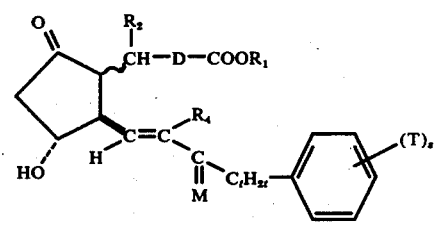

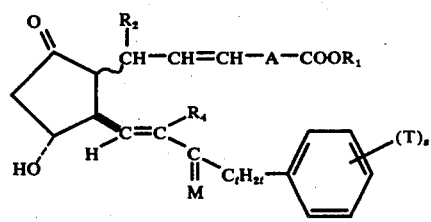

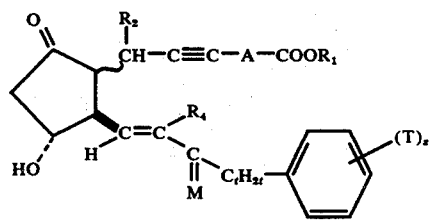

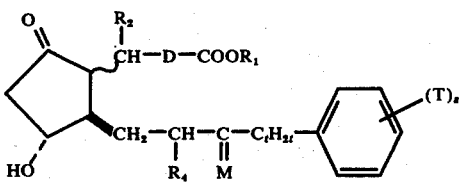

Formulas XI to XIV represent phenyl-substituted compounds of the PGE type.

In Formulas XI to XIV, $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or ethyl substituted in the β-position with 3 chloro, 2 or 3 bromo, or 1, 2, or 3 iodo. M is

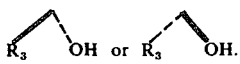

$R_2$, $R_3$, and $R_4$ are hydrogen or alkyl of one to 4 carbon atoms, inclusive. The moiety —$C_tH_{2t}$—represents (a) a valence bond or (b) alkylene of one to 10 carbon atoms, inclusive, substituted with zero, one, or 2 fluoro, with one to 7 carbon atoms, inclusive, between

and the ring. When one or 2 fluoro are present as substituents of —$C_tH_{2t}$, that moiety will contain 2t-1 or 2t-2 hydrogen atoms, respectively, rather than 2t hydrogen atoms. The symbol T represents alkyl of one to 4 carbon atoms, inclusive, fluoro, chloro, trifluoromethyl, or —$OR_9$, wherein $R_9$ is hydrogen or alkyl of one to 4 carbon atoms, inclusive. The symbol s represents zero, one, 2, or 3. Regarding the combination (T)$_s$ attached to the phenyl ring, no more than two T's are other than alkyl. Except for that proviso, when two or three T's are present as substituents, they are the same or different. The symbol D represents alkylene of 3 to 12 carbon atoms, inclusive, substituted with zero, one, 2, 3, or 4 fluoro, with 3 to 7 carbon atoms, inclusive, between —$CHR_2$— and $COOR_1$, and with the proviso that when 3 or 4 fluoro are present, they are all substituents of the carbon atoms alpha and beta to $COOR_1$. The symbol A represents alkylene of one to 10 carbon atoms, inclusive, substituted with zero, one, 2, 3, or 4 fluoro, with one to 5 carbon atoms, inclusive, between =CH— or ≡C— and —$COOR_1$, and with the proviso that when 3 or 4 fluoro are present, they are all substituents of the carbon atoms alpha and beta to —$COOR_1$.

The wavy line ~ in Formulas XI to XIV indicates attachment of the hydroxyl or the side chain to the cyclopentane ring in alpha or beta configuration.

Formulas XI to XIV include the separate isomers wherein M is either

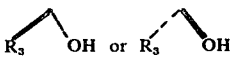

i.e., where the side chain hydroxy is in either S (alpha) or R (epi or beta) configuration. Referring to the prostanoic acid atom numbering the point of attachment corresponds to C-15, and, herein regardless of the variation in the C-1 to C-7 carbon chain, these epimers are referred to as C-15 epimers.

Included in Formula XII are both the cis and the trans compounds with respect to the C-5 to C-6 carbon-carbon double bond in the carboxyl-terminated side chain. In all of the compounds containing the C-13 to C-14 double bond, that carbon-carbon double bond is in trans configuration, and the chain containing $R_4$ is attached to the cyclopentane ring in beta configuration in compounds encompassed by Formulas XI to XIV.

Formulas XI to XIV include lower alkanoates, and also pharmacologically acceptable salts when $R_1$ is hydrogen.

Like the natural prostaglandins described above, these novel phenyl-substituted prostaglandin compounds have several centers of asymmetry. The novel compounds of this invention include (a) compounds having the same configuration as naturally occurring prostaglandins and (b) racemic compounds of (a) plus optically active enantiomeric forms thereof. As discussed hereinabove, two structural formulas are required to define accurately these racemic compounds. Formulas XI through XXVI, inclusive, are intended to represent optically active prostanoic acid analogs having the same absolute configuration as the naturally-occurring prostaglandins. However, for convenience in the charts herein only a single formula is used to define not only the optically active form but also the racemic compounds which generally undergo the same reactions.

Formula XI represents 17-phenyl-18,19,20-trinor-$PGE_1$ (Formula IX above) when $R_1$, $R_2$, $R_3$, and $R_4$ are each hydrogen, D is pentamethylene, $C_tH_{2t}$ is ethylene (t is 2), s is zero, the carboxyl-terminated side chain is attached to the cyclopentane ring in alpha configuration, and the configuration of the hydroxy in the

group is alpha (S).

In addition to the procedures incorporated by reference, including Charts C and D from the above-cited referenced application (or issued patent) the various $PGE_1$ and $PGF_1$ α type compounds are available by another route which may be preferred for convenience and availability of starting materials.

Chart M shows the steps by which compound LXXX is converted to a $PGE_1$ type analog of formula LXXXIII. Compounds of formula-LXXX are available by the process of Chart L or by obvious modifications thereof, such as esterification, to transform LXXIII into LXXX. In Chart M, the terms A, J, M, M', and Q have the same meaning as in Chart L. $R_1$ has the same definition as used throughout the specification.

In step (a), intermediate LXXX is reduced by catalytic hydrogenation to $PGF_1$ α type compound LXXXI. A preferred catalyst is 5% rhodium on alumina but other catalysts such as palladium and other carriers such as carbon are useful. The reaction is terminated when about one equivalent mole of hydrogen has been absorbed. Removal of blocking groups at J and M' yields $PGF_1$ type end products.

In step (b) compound LXXXI is oxidized to a $PGE_1$

CHART M

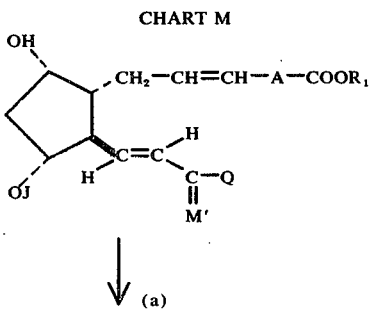

-continued

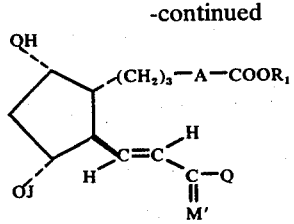

LXXXI (b)

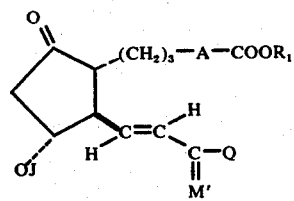

LXXXII (c)

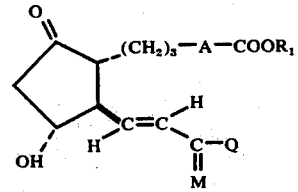

LXXXIII type compound LXXXII using procedures known in the art or described herein.

Finally in step (c) the blocking groups at J and M' are removed to yield the PGE$_1$ type end products. For example when J is tetrahydropyranyl mild acid hydrolysis is employed.

In addition to or supplementing the methods of administration incorporated by reference from the above-cited application (or issued patent), these compounds are effectively administered to human asthma patients by oral inhalation or by aerosol inhalation.

For administration by the oral inhalation route with conventional nebulizers or by oxygen aerosolization it is convenient to provide the instant active ingredient in dilute solution, preferably at concentrations of about 1 part of medicament to from about 100 to 200 parts by weight of total solution. Entirely conventional additives may be employed to stabilize these solutions or to provide isotonic media, for example, sodium chloride, sodium citrate, citric acid, sodium bisulfite, and the like can be employed.

For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can be used a dispersing agent such as oleyl alcohol. Suitable means to employ the aerosol inhalation therapy technique are described fully in U.S. Pat. No. 2,868,691, for example.

DESCRIPTION OF THE PREFERRED EMBODIMENTS

The following Preparations and Examples are in addition to those incorporated by reference from the above-cited application (or issued patent).

Example 269

16-Phenyl-17,18,19,20-tetranor-PGE$_2$(Formula XII: A is —(CH$_2$)$_3$—; R$_1$, R$_2$, R$_3$, and R$_4$ are hydrogen; C$_t$H$_{2t}$ is —CH$_2$—; s is zero; —OH on —CR$_3$OH is in alpha configuration; and ~ is alpha).

Refer to Chart L and Examples 178-182 inclusive.

I. The formula-LXXVII aldehyde obtained following the procedure of Preparation 8 from 1 g. of the optically active hydroxymethyl compound is diluted with 25 ml. of benzene and treated with the phosphorane of Preparation 11, namely 2-oxo-3-phenylpropyltriphenylphosphorane (3.6 g.). The mixture is stirred for one hr., washed with brine, dried, and concentrated. Silica gel chromatography yields about 200 mg. of the formula-LXXVIII product. An analytical sample obtained by crystallizing from ethyl acetate has m.p. 130.5°–132° C.

II. the product of Part I is reduced to the 3'α and 3'β hydroxy compounds of formula LXXIX following the procedure of Example 178, with separation of the isomers by silica gel chromatography.

III. Thereafter, following the procedures of Examples 179 and 180 but using the 3'α product of part II, there is obtained the formula-LXXIII compound, namely 16-phenyl-17,18,19,20-tetranor-PGF$_{2\alpha}$, 11,15-bis(-tetrahydropyranyl) ether, 237 mg.

IV. Following the procedures of Example 182, the product of Part III is oxidized with Jones reagent to the formula-LXXV product.

Finally, the tetrahydropyranyl groups are removed by hydrolysis in tetrahydrofuran-water-acetic acid at 43° C. for one hr. and the product subjected to silica gel chromatography to yield the formula-XII title compound, 23 mg., having mass spectral peaks (TMS derivative) at 588 and 497.2634.

Preparation 13

Dimethyl 2-Oxo-3-phenylpropylphosphonate

A solution of dimethyl methylphosphonate (62 g.) in 400 ml. of tetrahydrofuran at —74° C. is treated by slow addition to 316 ml. of 1.6 M n-butyllithium in hexane, while maintaining the temperature below —62° C. A solution of phenylacetic acid, methyl ester (37.5 g.) in 100 ml. of tetrahydrofuran is added while maintaining the temperature below —60° C. The mixture is stirred at that temperature for 3 hr. and then allowed to warm to about 25° C. Acetic acid (30 g.) is added and the resulting precipitate removed by filtration. The filtrate is concentrated, taken up in diethyl ether, washed with water and brine, dried over magnesium sulfate and concentrated to the product, 38.74 g. The product is further distilled 140°–155° C./0.4 mm. to yield 19.5 g. of the title compound.

Example 270

16-Phenyl-17,18,19,20-tetranor-PGE$_2$ (Formula XXI: as defined in Example 269)

Refer to Chart L and Examples 177-182 inclusive.

I. Following the procedures of Example 177 but employing dimethyl 2-oxo-3-phenylpropylphosphonate (Preparation 13, 13.45 g.) instead of dimethyl 2-oxo-4-phenylbutylphosphonate, there is obtained the corresponding formula-LXXVIII compound namely 2-hydroxy-4-benzoxy-5-(1'-trans-3'-oxo-4'-phenyl-butenyl)cyclopentanyl acetic acid γ-lactone, having m.p. 126°–128° C.

II. Following the procedures of Example 178 but continuing with the compound of Part I above there are obtained the corresponding 3'α-hydroxy and 3'β-hydroxy formula LXXIX compounds. Starting with 43.9 g. of the formula-LXXVIII 3'-oxo compound, there are obtained, after silica gel chromatography, the formula-LXXIX compound namely 2-hydroxy-4-benzoxy-5(1'-trans-3'α-hydroxy-4'-phenyl-butenyl)cyclopentanyl acetic acid γ-lactone, 20.0 g., less polar than the 3'β-hydroxy compound.

III. Following the procedures of Example 179 but continuing with the 3'α-hydroxy compound of Part II above, there is first obtained the corresponding benzoate-free compound, 12.7 g.

Next, on reaction with dihydropyran, there is obtained the formula-LXXI compound, namely 2,4-dihydroxy-5(1'-trans-3'α-hydroxy-4-phenyl-butenyl)cyclopentyl acetic acid γ-lactone, 4,3'-bis(tetrahydropyranyl) ether, 18.592 g.

Thereafter, reduction with diisobutylaluminum hydride yields the formula-LXXII lactol, namely 2,4-dihydroxy-5-(1'-trans-3'α-hydroxy-4-phenyl-butenyl)cyclopentyl acetaldehyde γ-lactol, 4,3'-bis(tetrahydropyranyl)ether, 19 g.

IV. Following the procedures of Example 180, but continuing with the lactol of Part III above, there is obtained the formula-LXXIII product of the Wittig reaction, namely 16-phenyl-17,18,19,20-tetranor-PGF$_{2\alpha}$, 4,3'-bis(tetrahydropyranyl) ether, 18.588 g.

V. Following the procedures of Example 182, but continuing with the formula-LXXIII compound of Part IV, oxidation with Jones reagent yields the formula-LXXV compound, namely 16-phenyl-17,18,19,20-tetranor-PGE$_2$, 4,3'-bis-(tetrahydropyranyl) ether.

Thereafter, hydrolysis in tetrahydrofuran-acetic acid-water at 40° C. for 2 hrs., followed by silica gel chromatography yields the title compound, 0.3 g. The compound is crystallized from ethyl acetate-hexane, 0.2 g., m.p. 88°–89° C.

Example 271

16-Phenyl-17,18,19,20-tetranor-PGE$_1$, Methyl Ester (Formula XI: D is —(CH$_2$)$_5$—, M is

$C_tH_{2t}$ is methylene, $R_1$ is methyl, $R_2$ and $R_4$ are hydrogen, s is zero, and ~ is alpha)

Refer to Chart M.

I. The formula-LXXX compound, 16-phenyl-17,18,19,20-tetranor-PGF$_{2\alpha}$, 4,3'-bis(tetrahydropyranyl) ether, methyl ester is prepared from the corresponding formula-LXXX free acid (Example 269, 5.0 g.) by reaction with iodomethane (24.7 g.) in 80 ml. of acetonitrile in the presence of diisopropylethylamine (4.0 g.). The mixture is left at about 25° C. for 16 hr. and from it is recovered the methyl ester, 5.03 g., having R$_f$ 0.52 (TLC on silica gel in 10% acetone-dichloromethane).

II. The hydrogenation of LXXX (6.033 g.) to yield LXXXI is done at about 25° C. in ethyl acetate using 100 mg. of 5% rhodium-on-alumina and terminating when about 10% over the theoretical one mole equivalent of hydrogen has been taken up. The product is a clear liquid, 5.374 g.

III. The formula-LXXXI intermediate (2.23 g.) is oxidized to the formula-LXXXII compound with chromium trioxide (2.16 g.) and pyridine (3.52 g.) in 55 ml. of dichloromethane at about 25°–28° C. for 20 min. The mixture is quenched with 43 ml. of 1N potassium hydrogen sulfate and ice and filtered. The filtrate is washed with water, dried over sodium sulfate and concentrated. The residue, 2.338 g., is subjected to silica gel chromatography, eluting with 5% acetone in dichloromethane to obtain the formula-LXXXII compound, 2.111 g.

IV. The above formula-LXXXII intermediate (2.111 g.) is hydrolyzed in a mixture of 10 ml. of tetrahydrofuran, 30 ml. of water, and 60 ml. of acetic acid at 40° C. for 4 hr. It is diluted with 200 ml. of water and freeze-dried. The resulting solid foam is dissolved in 200 ml. of diethyl ether, and the solution is washed with 1 N potassium bicarbonate and brine, dried over magnesium sulfate and concentrated to 1.302 g. Silica gel chromatography yields the title compound, 0.78 g. from the most polar fractions. The product is crystallized from acetone, 0.548 g., m.p. 73°–75° C., having R$_f$ 0.45 (TLC on silica gel in 40% acetone—60% dichloromethane, and having mass spectral peaks at (TMS derivative) at 517.2799, 514, 501, 441, 427, 423, 411, 351, 297, and 91.

Example 272

Self-propelled Aerosol Dosage Form

The procedure of U.S. Pat. No. 2,868,691 is used to prepare the instant compositions in self-propelling dosage unit forms.

A suitable measured quantity of the medicament is mixed with, and dissolved in, a measured amount of the cosolvent. A stabilizer, if desired, is added. A measured quantity of the resulting solution is then introduced into an open container. The open container and its contents are then cooled, preferably to a temperature below the boiling point of the propellant to be employed. A temperature of −25° F. is usually satisfactory. A measured quantity of the liquified propellant which also has been cooled below its boiling point is then introduced into the container and mixed with the solution already present. The quantities of the components introduced into the container are calculated to provide the desired concentration in each of the final compositions. Without permitting the temperature of the container and its contents to rise above the boiling point of the propellant, the container is sealed with a closure equipped with a suitable dispensing valve arrangement. Upon warming to room temperature the contents of the container are mixed by agitation of the container to insure complete solution of the medicament. The sealed container is then ready to dispense the composition and provide the medicament in aerosol form.

Nebulizing units each containing 15 ml. are filled according to the manipulative procedure described above with the following compositions:

| Composition 1 | Percent |
|---|---|
| 16-Phenyl-17,18,19,20-tetranor-PGE$_1$ | 0.25 |
| Ethanol | 34.75 |
| Dichlorodifluoromethane | 65.00 |
| Total | 100.00 |

| Compositions 2 and 3 | Percent | |
|---|---|---|
| 16-Phenyl-17,18,19,20-tetranor-PGE$_2$ | 0.25 | 0.25 |
| Ethanol | 34.75 | 34.75 |
| Dichlorotetrafluoroethane | 40 | 45.5 |
| Dichlorodifluoromethane | 25 | 19.5 |
| Total | 100.00 | 100.00 |

These packages when adjusted to deliver 300 single oral inhalations provide a single dose of 125 micrograms. A single inhalation is administered to control an acute brochial spasm. If necessary, after a full minute has elapsed, a second inhalation can be administered.

COMPOSITIONS 4–6

Prepared following the procedures for compositions 1-3, except that, instead of 16-phenyl-17,18,19,20-tetranor-PGE$_1$ or -PGE$_2$, the methyl esters of those compounds are used.

I claim:

1. An optically active compound of the formula:

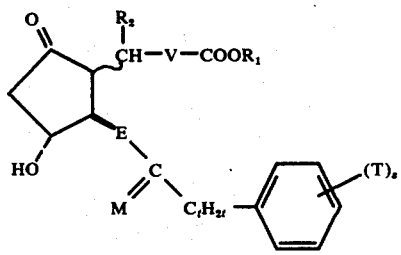

or a racemic compound of that formula and the mirror image thereof, wherein E is —CH$_2$CHR$_4$ — or trans —CH=CR$_4$—; wherein R$_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one, 2 or 3 chloro or alkyl of one to 4 carbon atoms, inclusive, or ethyl substituted in the β-position with 3 chloro, wherein M is

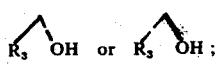

wherein R$_2$, R$_3$, and R$_4$ are hydrogen or alkyl of one to 4 carbon atoms, inclusive; wherein C$_t$H$_{2t}$ represents a valence bond or alkylene of one to 10 carbon atoms, inclusive, substituted with zero, one, or 2 fluoro, with one to 7 carbon atoms, inclusive, between

and the phenyl ring; wherein T is alkyl of one to 4 carbon atoms, inclusive, fluoro, chloro, trifluoromethyl, or —OR$_9$, wherein R$_9$ is hydrogen or alkyl of one to 4 carbon atoms, inclusive, and s is zero, one, 2, or 3, with the proviso that not more than two T's are other than alkyl; wherein V is (a) alkylene of 3 to 12 carbon atoms, inclusive, substituted with zero, one, 2, 3, or 4 fluoro, with 3 to 7 carbon atoms, inclusive, between —CHR$_2$ — and COOR$_1$, with the proviso that when 3 or 4 fluoro are present, they are all substituents of the carbon atoms alpha and beta to —COOR$_1$, (b) —CH=CH—A—, cis or trans, or (c) —C≡C—A—, wherein A is alkylene of one to 10 carbon atoms, inclusive, substituted with zero, one, 2, 3, or 4 fluoro, with one to 5 carbon atoms, inclusive, between =CH— (or C—) and —COOR$_1$, with the proviso that when 3 or 4 fluoro are present, they are all substituents of the carbon atoms alpha and beta to —COOR$_1$, with the further proviso that when E is —CH$_2$—CHR$_4$—V is (a) above; and wherein ~ indicates attachment of the group to the cyclopentane ring in alpha or beta configuration; including the lower alkanoates thereof, and the pharmacologically acceptable salts thereof when R$_1$ is hydrogen.

2. 2a,2b-Dihomo-17-phenyl-18,19,20-trinor-PGE$_2$, a compound according to claim 1.

3. 2a,2b-Dihomo-17-phenyl-18,19,20-trinor-PGE$_2$, methyl ester, a compound according to claim 1.

4. 17-Phenyl-2,18,19,20-tetranor-PGE$_2$, methyl ester, a compound according to claim 1.

5. A compound according to claim 1, wherein R$_2$ and R$_4$ are hydrogen, wherein the group

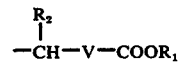

is attached to the cyclopentane ring in alpha configuration, and wherein V is (a) —(CH$_2$)$_a$—X—, (b) —CH=CH—(CH$_2$)$_b$—X—, or (c) —C≡C—(CH$_2$)$_b$—X—, wherein a is one, 2,3,4,or 5, b is zero, one, 2, or 3, and X is ethylene substituted by one, 2, 3, or 4 fluoro, methyl, or ethyl, or by one alkyl of 3 or 4 carbon atoms.

6. A compound according to claim 5 wherein a is 3 and b is one.

7. 2,2-Difluoro-17-phenyl-18,19,20-trinor-PGE$_2$, methyl ester, a compound according to claim 6.

8. 3-Methyl-17-phenyl-18,19,20-trinor-PGE$_2$, methyl ester, compounds according to claim 6.

9. 15(S)-15-Methyl-2,2-difluoro-17-phenyl-18,19,20-trinor-PGE$_2$, methyl ester, a compound according to claim 6.

10. A compound according to claim 1 wherein R$_2$ and R$_4$ are hydrogen, wherein the group

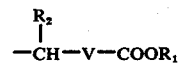

is attached to the cyclopentane ring in alpha configuration, and wherein V is (a) alkylene of 3 to 12 carbon atoms, inclusive, substituted with zero, one, 2,3, or 4 fluoro, with 5 carbon atoms in the chain between —CHR$_2$—and —COOR$_1$, (b) —CH=CH—A—, cis or trans, or (c) —C≡C—A—, wherein A is alkylene of one to 10 carbon atoms, inclusive, substituted with zero, one, 2, 3, or 4 fluoro, with 3 carbon atoms in the chain between =CH—(or ≡C—) and —COOR$_1$.

11. A compound according to claim 10 wherein $C_tH_{2t}$ is limited to one to 4 carbon atoms in the chain between

and the phenyl ring.

12. A compound according to claim 11 wherein V is alkylene of 3 to 12 carbon atoms, inclusive, substituted with zero, one, 2, 3, or 4 fluoro, with 5 carbon atoms in the chain between —$CHR_2$— and —$COOR_1$; and wherein E is trans—CH=CH—.

13. A compound according to claim 12 wherein M is

14. A compound according to claim 13 wherein $R_3$ is hydrogen.

15. A compound according to claim 14 wherein $C_tC_{2t}$ is methylene.

16. A compound according to claim 15 wherein $R_1$ is hydrogen, and the pharmacologically acceptable salts thereof.

17. 16-Phenyl-17,18,19,20-tetranor-$PGE_1$, a compound according to claim 16.

18. A compound according to claim 15 wherein $R_1$ is alkyl of one to 8 carbon atoms, inclusive.

19. 16-Phenyl-17,18,19,20-tetranor-$PGE_1$, methyl ester, a compound according to claim 18.

20. A compound according to claim 14 wherein $C_tH_{2t}$ is ethylene.

21. A compound according to claim 20 wherein $R_1$ is hydrogen, and the pharmacologically acceptable salts thereof.

22. 17-Phenyl-18,19,20-trinor-$PGE_1$, a compound according to claim 21.

23. A compound according to claim 20 wherein $R_1$ is alkyl of one to 8 carbon atoms, inclusive.

24. 17-Phenyl-18,19,20-trinor-$PGE_1$, methyl ester, a compound according to claim 23.

25. A compound according to claim 14 wherein $C_tH_{2t}$ is

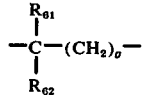

wherein g is zero, one, 2, or 3, and wherein $R_{61}$ and $R_{62}$ are hydrogen, alkyl of one to 4 carbon atoms, inclusive, or fluoro, being the same or different, with the proviso that $R_{62}$ is fluoro only when $R_{61}$ is hydrogen or fluoro, and with the further proviso that $R_{61}$ and $R_{62}$ are not both hydrogen.

26. A compound according to claim 25 wherein $R_{61}$ and $R_{62}$ are alkyl of one to 4 carbon atoms, inclusive.

27. A compound according to claim 26 wherein $C_tH_{2t}$ is —$(CH_3)_2$—$CH_2$—.

28. A compound according to claim 27 wherein $R_1$ is hydrogen, and the pharmacologically acceptable salts thereof.

29. 16,16-Dimethyl-17-phenyl-18,19,20-trinor-$PGE_1$, methyl ester, a compound according to claim 28.

30. A compound according to claim 27 wherein $R_1$ is alkyl of one to 8 carbon atoms, inclusive.

31. 16,16-Dimethyl-17-phenyl-18,19,20-trinor-$PGE_1$, methyl ester, a compound according to claim 30.

32. A compound according to claim 14 wherein $C_tH_{2t}$ is trimethylene.

33. A compound according to claim 32 wherein $R_1$ is hydrogen, and the pharmacologically acceptable salts thereof.

34. 18-Phenyl-19,20-dinor-$PGE_1$, a compound according to claim 33.

35. A compound according to claim 32 wherein $R_1$ is alkyl of one to 8 carbon atoms, inclusive.

36. 18-Phenyl-19,20-dinor-$PGE_1$, methyl ester, a compound according to claim 35.

37. A compound according to claim 13 wherein $R_3$ is methyl.

38. A compound according to claim 37 wherein $C_tH_{2t}$ is methylene.

39. A compound according to claim 38 wherein $R_1$ is hydrogen and the pharmacologically acceptable salts thereof.

40. 15(S)-15-Methyl-16-phenyl-17,18,19,20-tetranor-$PGE_1$, a compound according to claim 39.

41. A compound according to claim 38 wherein $R_1$ is alkyl of one to 8 carbon atoms, inclusive.

42. 15(S)-15-Methyl-16-phenyl-17,18,19,20-tetranor-$PGE_1$, methyl ester, a compound according to claim 41.

43. A compound according to claim 37 wherein $C_tH_{2t}$ is ethylene.

44. A compound according to claim 43 wherein $R_1$ is hydrogen; and the pharmacologically acceptable salts thereof.

45. 15(S)-15-Methyl-17-phenyl-18,19,20-trinor-$PGE_1$, a compound according to claim 44.

46. A compound according to claim 43 wherein $R_1$ is alkyl of one to 8 carbon atoms, inclusive.

47. 15(S)-15-Methyl-17-phenyl-18,19,20-trinor-$PGE_1$, methyl ester, a compound according to claim 46.

48. A compound according to claim 37 wherein $C_tH_{2t}$ is trimethylene.

49. A compound according to claim 48 wherein $R_1$ is hydrogen, and the pharmacologically acceptable salts thereof.

50. 15(S)-15-Methyl-18-phenyl-19,20-dinor-$PGE_1$, a compound according to claim 49.

51. A compound according to claim 48 wherein $R_1$ is alkyl of one to 8 carbon atoms, inclusive.

52. 15(S)-15-Methyl-18-phenyl-19,20-dinor-$PGE_1$, a compound according to claim 51.

53. A compound according to claim 12 wherein M is

54. A compound according to claim 53 wherein $R_3$ is hydrogen.

55. A compound according to claim 53 wherein $R_3$ is methyl.

56. A compound according to claim 55 wherein $C_tH_{2t}$ is ethylene.

57. A compound according to claim 56 wherein $R_1$ is hydrogen, and the pharmacologically acceptable salts thereof.

58. 15(R)-15-Methyl-17-phenyl-18,19,20-trinor-PGE$_1$, a compound according to claim 57.
59. A compound according to claim 56 wherein R$_1$ is alkyl of one to 8 carbon atoms, inclusive.
60. 15(R)-15-Methyl-17-phenyl-18,19,20-trinor-PGE$_1$, methyl ester, a compound according to claim 59.
61. A compound according to claim 11 wherein V is —CH=CH—A—, cis or trans, wherein a is alkylene of one to 10 carbon atoms, inclusive, substituted with zero, one, 2, 3, or 4 fluoro, with 3 carbon atoms in the chain between =CH— and —COOR$_1$; and wherein E is trans—CH=CH—.
62. A compound according to claim 61 wherein M is

63. A compound according to claim 62 wherein R$_3$ is hydrogen.
64. A compound according to claim 63 wherein C$_t$H$_{2t}$ is methylene.
65. A compound according to claim 64 wherein R$_1$ is hydrogen, and the pharmacologically acceptable salts thereof.
66. 16-Phenyl-17,18,19,20-tetranor-PGE$_2$, a compound according to claim 65.
67. A compound according to claim 64 wherein R$_1$ is alkyl of one to 8 carbon atoms, inclusive.
68. 16-Phenyl-17,18,19,20-tetranor-PGE$_2$, methyl ester, a compound according to claim 67.
69. A compound according to claim 63 wherein C$_t$H$_{2t}$ is ethylene.
70. A compound according to claim 69 wherein R$_1$ is hydrogen, and the pharmacologically acceptable salts thereof.
71. 17-Phenyl-18,19,20-trinor-PGE$_2$, a compound according to claim 70.
72. 17-(p-Chlorophenyl)-18,19,20-trinor-PGE$_2$, a compound according to claim 70.
73. 17-(p-Fluorophenyl)-18,19,20-trinor-PGE$_2$, a compound according to claim 70.
74. A compound according to claim 69 wherein R$_1$ is alkyl of one to 8 carbon atoms, inclusive.
75. 17-Phenyl-18,19,20-trinor-PGE$_2$, methyl ester, a compound according to claim 74.
76. 17-(p-Chlorophenyl)-18,19,20-trinor PGE$_2$, methyl ester, a compound according to claim 74.
77. 17-(p-Chlorophenyl)-18,19,20-trinor-PGE$_2$, ethyl ester, a compound according to claim 74.
78. A compound according to claim 63 wherein C$_t$H$_{2t}$ is

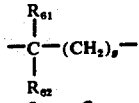

wherein g is zero, one, 2, or 3, and wherein R$_{61}$ and R$_{62}$ are hydrogen, alkyl of one to 4 carbon atoms, inclusive, or fluoro, being the same or different, with the proviso that R$_{62}$ is fluoro only when R$_{61}$ is hydrogen or fluoro, and with the further proviso that R$_{61}$ and R$_{62}$ are not both hydrogen.
79. A compound according to claim 78 wherein R$_{61}$ and R$_{62}$ are alkyl of one to 4 carbon atoms, inclusive.
80. A compound according to claim 79 wherein C$_t$H$_{2t}$ is -C(CH$_3$)$_2$-CH$_2$-.

81. A compound according to claim 80 wherein R$_1$ is hydrogen, and the pharmacologically acceptable salts thereof.
82. 16,16-Dimethyl-17-phenyl-18,19,20-trinor-PGE$_2$, a compound according to claim 81.
83. A compound according to claim 80 wherein R$_1$ is alkyl of one to 8 carbon atoms, inclusive.
84. 16,16-Dimethyl-17-phenyl-18,19,20-trinor-PGE$_2$, methyl ester, a compound according to claim 83.
85. A compound according to claim 63 wherein C$_t$H$_{2t}$ is trimethylene.
86. A compound according to claim 85 wherein R$_1$ is hydrogen, and the pharmacologically acceptable salts thereof.
87. 18-Phenyl-19,20-dinor-PGE$_2$, a compound according to claim 86.
88. A compound according to claim 85 wherein R$_1$ is alkyl of one to 8 carbon atoms, inclusive.
89. 18-Phenyl-19,20-dinor-PGE$_2$, methyl ester, a compound according to claim 88.
90. A compound according to claim 62 wherein R$_3$ is methyl.
91. A compound according to claim 90 wherein C$_t$H$_{2t}$ is methylene.
92. A compound according to claim 91 wherein R$_1$ is hydrogen, and the pharmacologically acceptable salts thereof.
93. 15(S)-15-Methyl-16-phenyl-17,18,19,20-tetranor-PGE$_2$, a compound according to claim 92.
94. A compound according to claim 91 wherein R$_1$ is alkyl of one to 8 carbon atoms, inclusive.
95. 15(S)-15-Methyl-16-phenyl-17,18,19,20-tetranor-PGE$_2$, methyl ester, a compound according to claim 94.
96. A compound according to claim 90 wherein C$_t$H$_{2t}$ is ethylene.
97. A compound according to claim 96 wherein R$_1$ is hydrogen, and the pharmacologically acceptable salts thereof.
98. 15(S)-15-Methyl-17-phenyl-18,19,20-trinor-PGE$_2$, a compound according to claim 97.
99. A compound according to claim 96 wherein R$_1$ is alkyl of one to 8 carbon atoms, inclusive.
100. 15(S)-15-Methyl-17-phenyl-18,19,20-trinor-PGE$_2$, methyl ester, a compound according to claim 99.
101. A compound according to claim 90 wherein C$_t$H$_{2t}$ is trimethylene.
102. A compound according to claim 101 wherein R$_1$ is hydrogen, and the pharmacologically acceptable salts thereof.
103. 15(S)-15-Methyl-18-phenyl-19,20-dinor-PGE$_2$, a compound according to claim 102.
104. A compound according to claim 101 wherein R$_1$ is alkyl of one to 8 carbon atoms, inclusive.
105. 15(S)-15-Methyl-18-phenyl-19,20-dinor-PGE$_2$, methyl ester, a compound according to claim 104.
106. A compound according to claim 61 wherein M is

107. A compound according to claim 106 wherein R$_3$ is hydrogen.
108. A compound according to claim 106 wherein R$_3$ is methyl.

109. A compound according to claim 108 wherein $C_tH_{2t}$ is ethylene.

110. A compound according to claim 109 wherein $R_1$ is hydrogen, and the pharmacologically acceptable salts thereof.

111. 15(R)-15-Methyl-17-phenyl-18,19,20-trinor-PGE$_2$, a compound according to claim 110.

112. A compound according to claim 109 wherein $R_1$ is alkyl of one to 8 carbon atoms, inclusive.

113. 15(R)-15-Methyl-17-phenyl-18,19,20-trinor-PGE$_2$, methyl ester, a compound according to claim 112.

114. A compound according to claim 11 wherein V is —C≡C—A—, wherein A is alkylene of one to 10 carbon atoms, inclusive, substituted with zero, one, 2, 3, or 4 flouro, with 3 carbon atoms in the chain between ≡C— and —COOR$_1$; and wherein E is trans—CH=CH—.

115. A compound according to claim 114 wherein M is

116. A compound according to claim 115 wherein $R_3$ is hydrogen.

117. A compound according to claim 116 wherein $C_tH_{2t}$ is ethylene.

118. A compound according to claim 177 wherein $R_1$ is hydrogen, and the pharmacologically acceptable salts thereof.

119. 5,6-Didehydro-17-phenyl-18,19,20-trinor-PGE$_2$, a compound according to claim 118.

120. A compound according to claim 117 wherein $R_1$ is alkyl of one to 8 carbon atoms, inclusive.

121. 5,6-Didehydro-17-phenyl-18,19,20-trinor-PGE$_2$, methyl ester, a compound according to claim 120.

122. A compound according to claim 115 wherein $R_3$ is methyl.

123. A compound according to claim 122 wherein $C_tH_{2t}$ is ethylene.

124. A compound according to claim 123 wherein $R_1$ is hydrogen, and the pharmacologically acceptable salts thereof.

125. 5,6-Didehydro-15(S)-15-methyl-17-phenyl-18,19,20-trinor-PGE$_2$, a compound according to claim 124.

126. A compound according to claim 114 wherein M is

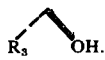

127. A compound according to claim 11 wherein V is alkylene of 3 to 12 carbon atoms, inclusive, substituted with zero, one, 2, 3, or 4 fluoro, with 5 carbon atoms in the chain between —CHR$_2$— and —COOR$_1$; and wherein E is —CH$_2$CH$_2$—.

128. A compound according to claim 127 wherein M is

129. A compound according to claim 128 wherein $R_3$ is hydrogen.

130. A compound according to claim 129 wherein $C_tH_{2t}$ is ethylene.

131. A compound according to claim 130 wherein $R_1$ is hydrogen, and the pharmacologically acceptable salts thereof.

132. 13,14-Dihydro-17-phenyl-18,19,20-trinor-PGE$_1$, a compound according to claim 131.

133. A compound according to claim 130 wherein $R_1$ is alkyl of one to 8 carbon atoms, inclusive.

134. 13,14-Dihydro-17-phenyl-18,19,20-trinor-PGE$_1$, methyl ester, a compound according to claim 133.

135. A compound according to claim 128 wherein $R_3$ is methyl.

136. A compound according to claim 135 wherein $C_tH_{2t}$ is ethylene.

137. A compound according to claim 136 wherein $R_1$ is hydrogen, and the pharmacologically acceptable salts thereof.

138. 13,14-Dihydro-15(S)-15-methyl-17-phenyl-18,19,20-trinor-PGE$_1$, a compound according to claim 137.

139. A compound according to claim 127 wherein M is

140. A bronchodilating and bronchial spasm reducing composition formulated for inhalation therapy as an aerosol such that each dose comprises:
  a. a bronchodilating and bronchial spasm reducing amount of a compound of the formula

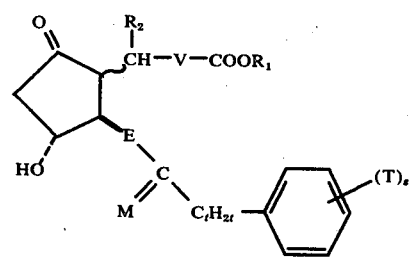

or a racemic compound of that formula and the mirror image thereof, wherein E is —CH$_2$CHR$_4$— or trans—CH=CR$_4$—; wherein $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or ethyl substituted in the β-position with 3 chloro; wherein M is

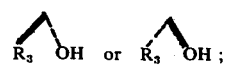

wherein $R_2$, $R_3$, and $R_4$ are hydrogen or alkyl of one to 4 carbon atoms, inclusive; wherein $C_tH_{2t}$ represents a valence bond or alkylene of one to 10 carbon atoms, inclusive, substituted with zero, one, or 2 fluoro, with one to 7 carbon atoms, inclusive, between

and the phenyl ring; wherein T is alkyl of one to 4 carbon atoms, inclusive, fluoro, chloro, trifluoromethyl, or —OR$_9$, wherein R$_9$ is hydrogen or alkyl of one to 4 carbon atoms, inclusive, and s is zero, one, 2, or 3, with the proviso that not more than two T's are other than alkyl; wherein V is (a) alkylene of 3 to 12 carbon atoms, inclusive, substituted with zero, one, 2, 3, or 4 fluoro, with 3 to 7 carbon atoms, inclusive, between —CHR$_2$— and COOR$_1$, with the proviso that when 3 or 4 fluoro are present, they are all substituents of the carbon atoms alpha and beta to —COOR$_1$, (b) —CH=CH—A—, cis or trans, or (c) —C≡C—A—, wherein A is alkylene of one to 10 carbon atoms, inclusive, substituted with zero, one, 2, 3 or 4 fluoro, with one to 5 carbon atoms, inclusive, between =CH— (or ≡C—) and —COOR$_1$, with the proviso that when 3 or 4 fluoro are present, they are all substituents of the carbon atoms alpha and beta to —COOR$_1$, with the further proviso that when E is —CH$_2$—CHR$_4$— V is (a) above; and wherein ~ indicates attachment of the group to the cyclopentane ring in alpha or beta configuration; including the lower alkanoates thereof, and the pharmacologically acceptable salts thereof when R$_1$ is hydrogen; and b. a pharmacologically-acceptable inhalation carrier, in an amount sufficient to provide a composition administerable by the oral inhalation route.

141. A self-propelled aerosol dosage form nebulizer unit for inhalation therapy consisting essentially of an aerosol container adapted to provide dosage unit form inhalation therapy containing an aerosol propellant and the composition of claim 140.

142. A composition as defined in claim 140 wherein said compound is 16-phenyl-17,18,19,20-tetranor-PGE$_2$.

143. A composition as defined in claim 140 wherein said compound is 16-phenyl-17,18,19,20-tetranor-PGE$_2$, methyl ester.

144. A method of relieving bronchial spasm and facilitating breathing in warm blooded animals which comprises administering to a warm blood animal in need thereof an amount sufficient to relieve bronchial spasm and facilitate breathing in said warm blood animal of a composition comprising a. a compound of the formula

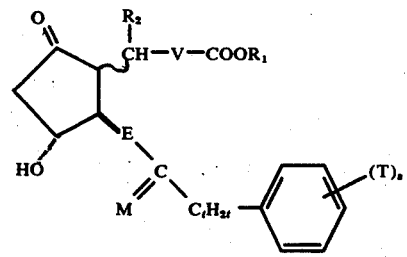

or a racemic compound of that formula and the mirror image thereof, wherein E is —CH$_2$CHR$_4$— or trans—CH=CR$_4$; wherein R$_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or ethyl substituted in the β-position with 3 chloro; wherein M is

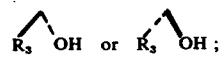

wherein R$_2$, R$_3$, and R$_4$ are hydrogen or alkyl of one to 4 carbon atoms, inclusive; wherein C$_t$H$_{2t}$ represents a valence bond or alkylene of one to 10 carbon atoms, inclusive, substituted with zero, one, or 2 fluoro, with one to 7 carbon atoms, inclusive, between

and the phenyl ring; wherein T is alkyl of one to 4 carbon atoms, inclusive, fluoro, chloro, trifluoromethyl, or —OR$_9$, wherein R$_9$ is hydrogen or alkyl of one to 4 carbon atoms, inclusive, and s is zero, one, 2, or 3, with the proviso that not more than two T's are other than alkyl; wherein V is (a) alkylene of 3 to 12 carbon atoms, inclusive, substituted with zero, one, 2, 3, or 4 fluoro, with 3 to 7 carbon atoms, inclusive, between —CHR$_2$— and COOR$_1$, with the proviso that when 3 or 4 fluoro are present, they are all substituents of the carbon atoms alpha and beta to —COOR$_1$, (b) —CH=CH—A—, cis or trans, or (c) —C≡C—A—, wherein A is alkylene of one to 10 carbon atoms, inclusive, substituted with zero, one, 2, 3 or 4 fluoro, with one to 5 carbon atoms, inclusive, between =CH (or ≡C$_{13}$) and—COOR$_1$, with the proviso that when 3 or 4 fluoro are present, they are all substituents of the carbon atoms alpha and beta to —COOR$_1$, with the proviso that when E is —CH$_2$—CHR$_4$— V is (a) above; and wherein ~ indicates attachment of the group to the cyclopentane ring in alpha or beta configuration; including the lower alkanoates thereof, and the pharmacologically acceptable salts thereof when R$_1$ is hydrogen; and b. a pharmacologically acceptable carrier.

145. A method as defined in claim 144 wherein said administering is by the oral inhalation route.

146. A method as defined in claim 144 wherein said administering is effected by the use of a self-propelled aerosol dosage form nebulizer unit.

147. A method as defined in claim 144 wherein said compound is 16-phenyl-17,18,19,20-tetranor-PGE$_2$.

148. A method as defined in claim 144 wherein said compound is 16-phenyl-17,18,19,20-tetranor-PGE$_2$, methyl ester.

* * * * *

UNITED STATES PATENT OFFICE
CERTIFICATE OF CORRECTION

Patent No. 4,029,814  Dated June 14, 1977

Inventor(s) Gordon L. Bundy

It is certified that error appears in the above-identified patent and that said Letters Patent are hereby corrected as shown below:

Column 10, line 13, "( or  C-)" should read -- (or $\equiv$C-) --.

Column 13, line 8, "a" should read -- A --.

Column 18, lines 48-9, "=CH (or $\equiv C_{13}$)" should read -- =CH- (or $\equiv$C-) --.

Column 4, line 52, "$PGF_1$ type" should read -- $PGF_{1\alpha}$ type --.

Signed and Sealed this

Fourteenth Day of February 1978

[SEAL]

Attest:

RUTH C. MASON  
Attesting Officer

LUTRELLE F. PARKER  
Acting Commissioner of Patents and Trademarks